US00PP25261P3

(12) United States Plant Patent
Dibley

(10) Patent No.: US PP25,261 P3
(45) Date of Patent: Jan. 27, 2015

(54) ***STREPTOCARPUS* PLANT NAMED 'SLSBC09-0'**

(50) Latin Name: ***Streptocarpus* hybrid**
Varietal Denomination: SLSBC09-0

(71) Applicant: Lynne Dibley, Ruthin (GB)

(72) Inventor: Lynne Dibley, Ruthin (GB)

(73) Assignee: Dibley's Nurseries (GB)

( * ) Notice: Subject to any disclaimer, the term of this patent is extended or adjusted under 35 U.S.C. 154(b) by 168 days.

(21) Appl. No.: 13/694,741

(22) Filed: Dec. 27, 2012

(65) Prior Publication Data

US 2014/0189920 P1 Jul. 3, 2014

(51) Int. Cl.
*A01H 5/00* (2006.01)

(52) U.S. Cl.
USPC ..... Plt./333

(58) Field of Classification Search
USPC ..... Plt./333
See application file for complete search history.

*Primary Examiner* — Kent L Bell
(74) *Attorney, Agent, or Firm* — Cassandra Bright

(57) ABSTRACT

A new and distinct *Streptocarpus* cultivar named 'SLSBC09-0' is disclosed, characterized by large flowers with purple-violet colored upper lobes and yellow lower lobes, with unique flower markings. Plants are highly floriferous. The new variety is a *Streptocarpus*, suitable as an outdoor garden or container plant.

2 Drawing Sheets

Figure 1:
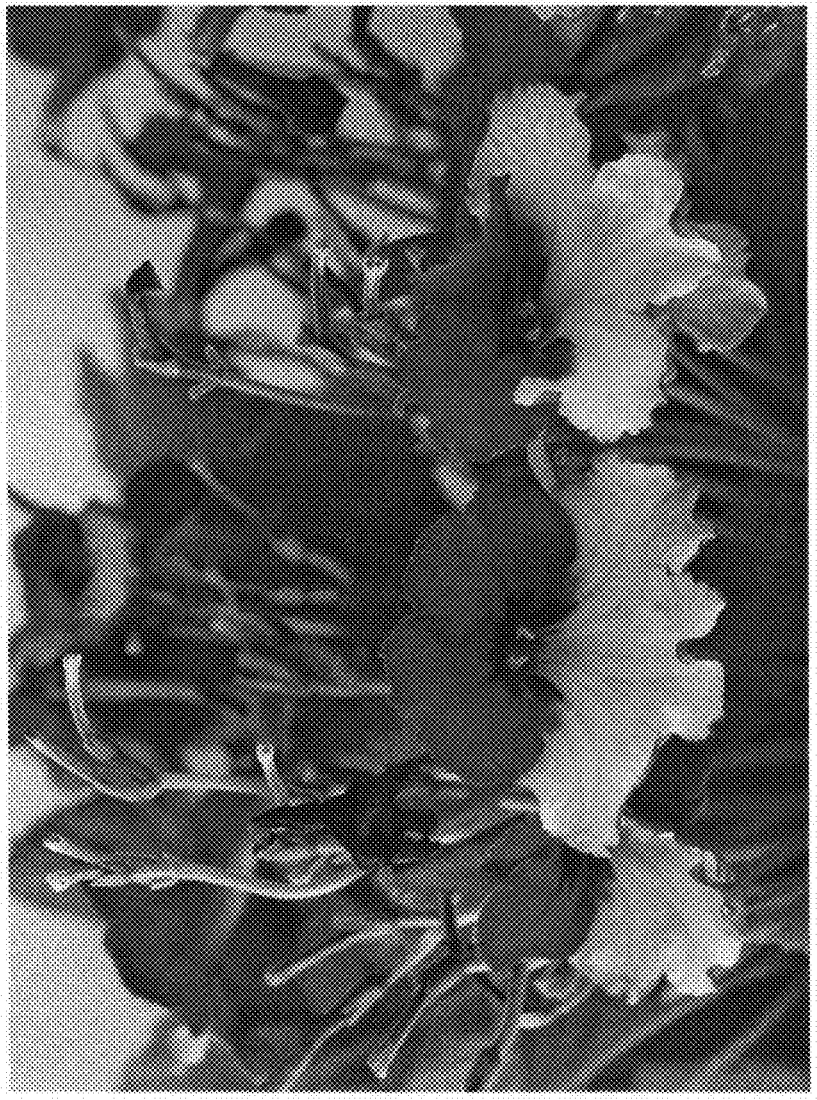

Latin name of the genus and species: *Streptocarpus* hybrid.
Variety denomination: 'SLSBC09-0'.

The new *Streptocarpus* cultivar is the product of a planned breeding program by the inventor Lynne Dibley, a citizen of United Kingdom. The breeding program was carried out at a commercial nursery in Ruthin, United Kingdom. The objective of the breeding program was to develop new *Streptocarpus* varieties for ornamental purposes.

The new variety resulted from the crossing of the seed parent, an unnamed, unpatented proprietary *Streptocarpus* seedling with the pollen parent, an unnamed, unpatented proprietary *Streptocarpus* seedling in 2008. The new variety was discovered in 2009 by the inventor in a group of seedlings resulting from the 2008 crossing, at a commercial nursery in Ruthin, United Kingdom.

Asexual reproduction of the new cultivar 'SLSBC09-0' by vegetative cuttings was first performed at a commercial greenhouse in Ruthin, United Kingdom in 2009. Subsequently at least five generations have been produced from vegetative cuttings, and have shown that the unique features of this cultivar are stable and reproduced true to type.

SUMMARY OF THE INVENTION

The cultivar 'SLSBC09-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SLSBC09-0'. These characteristics in combination distinguish 'SLSBC09-0' as a new and distinct *Streptocarpus* cultivar:

1. Large flowers size.
2. Pale purple-violet upper floral lobes.
3. Yellow lower 3 floral lobes.

4. High flower count per plant.
5. Unique flower markings.

COMPARISON TO THE PARENT VARIETIES

Plants of the new cultivar 'SLSBC09-0' are similar in most horticultural characteristics to plants of the unnamed, unpatented proprietary seed parent. However, the new variety has a smaller overall flower size and smaller leaves than the seed parent. Additionally, plants of 'SLSBC09-0' produce flowers of different color and markings than flowers of the seed parent.

Plants of the new cultivar 'SLSBC09-0' are similar in most horticultural characteristics to plants of the unnamed, unpatented proprietary pollen parent. However, the new variety has a larger overall flower size and larger leaves than the pollen parent. Additionally, plants of 'SLSBC09-0' produce different color upper lobes than the pollen parent.

COMPARISON TO COMMERCIAL VARIETY

The new cultivar can be compared to the commercial variety 'Harlequin Blue', unpatented. Plants of the two cultivars are similar in most horticultural characteristics, however, plants of 'SLSBC09-0' produce more and larger leaves as well as flowering later. Additionally, plants of 'SLSBC09-0' produce a longer peduncle and different colored upper floral lobes.

The new cultivar can be compared to the commercial variety 'Bethan', unpatented. Plants of the two cultivars are similar in most horticultural characteristics, however, plants of 'SLSBC09-0' produce no striping on flower lobes as well as flowering later. Additionally, plants of 'SLSBC09-0' produce a longer peduncle and different colored upper floral lobes.

BRIEF DESCRIPTION OF THE PHOTOGRAPHS

The accompanying photograph in FIG. 1 illustrates in full color a typical flower of 'SLSBC09-0'.

Figure 2:
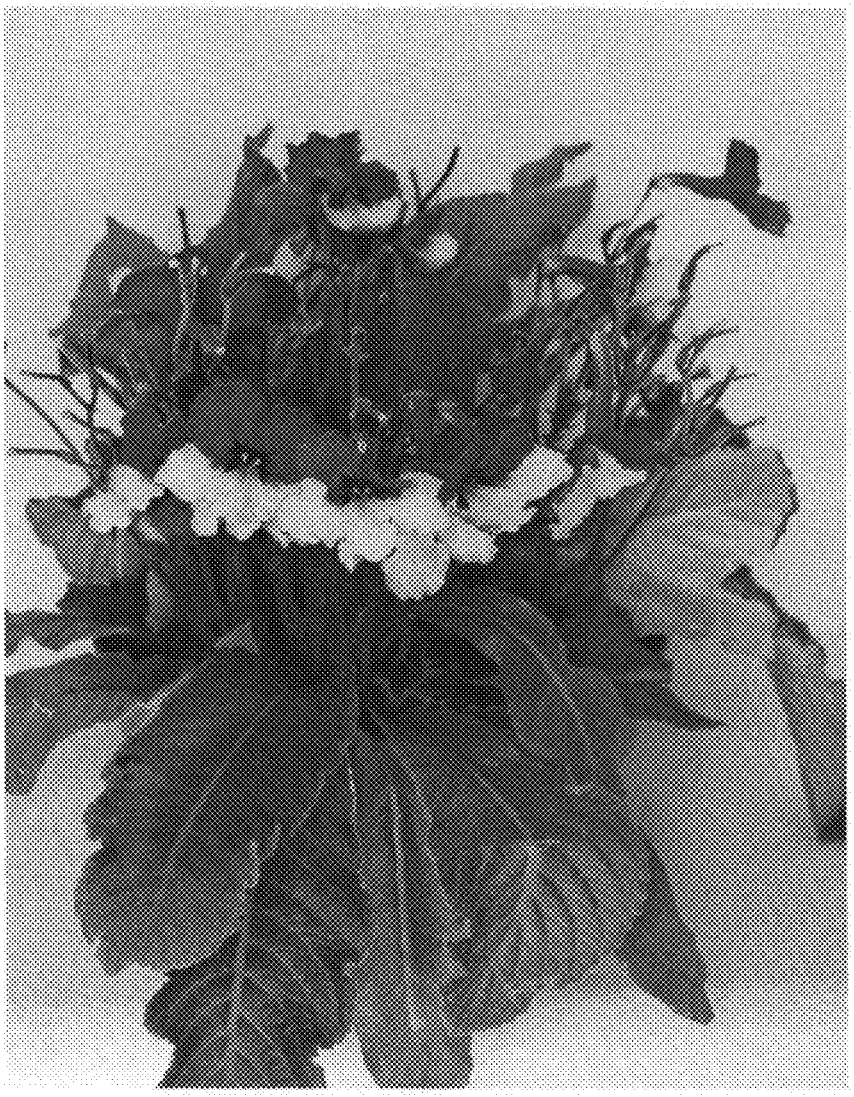

FIG. 2 illustrates a typical plant of 'SLSBC09-0' grown in a greenhouse, in a 10 inch commercial pot. Age of the plant photographed is approximately 30 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurement describe 'SLSBC09-0' plants grown in a commercial greenhouse in Oxnard, Calif. The growing temperature ranged from approximately 12° C. to 30° C. The greenhouse is subject to partial shade. General light conditions are bright, normal sunlight with some shade during the brightest part of the day. Measurements and numerical values represent averages of typical plant types.

Botanical classification: *Streptocarpus* hybrid 'SLSBC09-0'.

PROPAGATION

Time to initiate roots: About 20 to 25 days at approximately 21 to 25° C.

Root description: Fine, fibrous.

PLANT

Growth habit: Upright.

Age of the plant described: Approximately 30 weeks from a well rooted cutting.

Pot size of plant described: 8 inch pot.

Height: Approximately 17 cm from soil line to top of foliar plane. Approximately 20 cm to top of highest flower.

Plant spread: Approximately 42 cm at widest point.

Growth rate: Moderate.

Branching characteristics: Basal rosettes of foliate, no stem, no branches.

FOLIAGE

Leaf:

*Arrangement*.—Rosette.

*Quantity*.—Average 25 to 40 leaves.

*Average length*.—Approximately 20 cm.

*Average width*.—Approximately 7 cm.

*Shape of blade*.—Elliptic.

*Apex*.—Acute.

*Base*.—Attenuate.

*Margin*.—Crenate.

*Appearance of top surface*.—Matte.

*Appearance of top surface*.—Matte.

*Pubescence*.—Very short, less than 1 mm hairs, densely covering top and bottom leaf surfaces.

*Aspect*.—Undulating, overall leaf, including petiole, reflexes downward in older foliage.

*Color*.—Young foliage upper side: Near RHS Green 137A. Young foliage under side: Near RHS Green 138B. Mature foliage upper side: Near RHS Green 137B. Mature foliage under side: Near RHS Yellow-Green 144D.

*Venation*.—Type: Pinnate. Venation color upper side: Near RHS Green 143C. Venation color under side: Near RHS Yellow-Green 144D.

*Petiole*.—Not present, leaves sessile.

FLOWER

Natural flowering season: Continuous.

Inflorescence and flower type and habit: Racemes of 2 asymmetrical funnel shaped flowers.

Inflorescence longevity on plant: At least 2 weeks before any significant change is observed.

Approximate quantity of flowers per plant: Approximately 25 mature and immature flowers per plant.

Flowers persistent:

Inflorescence:

*Diameter of entire inflorescence*.—Approximately 7.0 cm.

*Depth of inflorescence*.—Approximately 8.0 cm.

Individual flower bud:

*Shape*.—Tubular, with spherical apex.

*Length*.—Approximately 3.0 cm.

*Diameter*.—Approximately 1.4 cm.

*Color*.—Near RHS Purple N79.

Flowers:

*Flower length*.—7.0 cm.

*Flower width*.—4.8 cm.

*Upper petals* (*upper lip*).—Number: 2, fused together at base. Length: 2.0 cm. Width: 2.5 cm. Shape: Obicular. Apex: Obtuse, ruffled. Margin: Shallow crenate. Texture: Velvety, all surfaces. Pubescent outersurface. Color: When opening: Inner surface: RHS Purple N79C. Outer surface: RHS Purple N79C. Fully opened: Inner surface: Near RHS Purple-Violet N81A. Outer surface: Near RHS Purple-Violet N81B. Aging: Inner surface: Near RHS Purple 77A. Outer surface: Near RHS Purple 77A.

*Lower petals* (*lower lip*).—Quantity: 3. Length: 2.0 cm. Width: 2.0 cm. Shape: Somewhat elongated orbicular, fused at base. Apex shape: Obtuse, with minutely shallow lobes. Ruffled appearance. Margin: Shallow crenate, undulating. Texture: Velvety, all surfaces. Pubescent outersurface. Color: When opening: Inner surface: RHS Yellow 10A. Outer surface: RHS Purple 77A. Fully opened: Inner surface: RHS Yellow 2C, very faint flushing near margin Purple 77B. Outer surface: RHS Purple 77A. Aging: Inner surface: RHS Green-Yellow 1A. Outer surface: RHS Purple N79C.

*Throat*.—Length: 3.5 cm. Width: 1 cm, at widest point. Texture: glabrous, shiny inner surface. Outer surface pubescent. Color: When opening: Inner surface: Striped, RHS White N155C and Purple N79A. Outer surface: RHS Purple N79B. Fully opened: Inner surface: Striped, RHS White N155C and Purple N79A. Outer surface: RHS Purple N79D. Aging: Inner surface: Striped, RHS White N155C and Purple N79A. Outer surface: RHS Purple N79D with faint streaks White N155C.

Sepals:

*Quantity*.—Average 5.

*Shape*.—Narrow deltate, base fused.

*Length*.—Approximately 0.5 cm.

*Width*.—Approximately 0.15 cm.

*Apex*.—Acute.

*Base*.—Fused.

*Margin*.—Entire.
*Texture*.—Highly pubescent, all surfaces.
*Color*.—Upper Surface: Near RHS Green 137A. Lower Surface: Near RHS Green 137A.

Peduncle:
*Length*.—Longest average 15 cm. Shortest average 6 cm.
*Diameter*.—Approximately 0.4 cm.
*Texture*.—Densely pubescent.
*Color*.—Near RHS Yellow-Green 144A.
*Orientation*.—Approximately 90 to 75 degree angle from rosette Moderate outward curvature on peduncles emerging farther from center.

Pedicel:
*Length*.—Average range 0.8 cm to 2.6 cm.
*Diameter*.—Approximately 0.3 cm.
*Texture*.—Soft, dense pubescence.
*Color*.—Near RHS Yellow-Green 144B.
*Orientation*.—Approximately 30 degree angle from peduncle. Straight, or slightly outwardly curved.

Fragrance: None.

REPRODUCTIVE ORGANS

Stamens:
*Number*.—2.
*Filament length*.—Approximately 0.7 cm, unfused section.

Anthers:
*Length*.—Approximately 0.2 cm.
*Shape*.—Bi-lobed.
*Color*.—Near RHS White 155B.
*Pollen*.—Not observed.

Pistil:
*Number*.—1.
*Length*.—Approximately 2.0 cm.
*Style*.—Length: Approximately 1.8 cm. Color: Near RHS Greyed-Purple N187B.
*Stigma*.—Shape: Bifurcate. Color: Near RHS Greyed-Purple N187C.

OTHER CHARACTERISTICS

Seeds and fruits: Not observed.

Disease/pest resistance: Neither resistant nor susceptible to normal diseases and pests of *Streptocarpus*.

Temperature tolerance: USDA zones 9-11.

What is claimed is:

1. A new and distinct cultivar of *Streptocarpus* plant named 'SLSBC09-0' as herein illustrated and described.

* * * * *